United States Patent
Hopkins et al.

(12)

(10) Patent No.: US 6,333,027 B1
(45) Date of Patent: Dec. 25, 2001

(54) COMPOSITION FOR TREATING AND/OR AMELIORATING THE DISEASES OF DANDRUFF, SEBORRHEIC DERMATITIS, PSORIASIS AND ECZEMA AND SYMPTOMS THEREOF

(75) Inventors: John Hopkins, Newbury (GB); Alain Khaiat, Singapore (SG); Noel D. Manigbas, Muntinlupa (PH); Elizabeth Wen Ping; Rex J. Baker, both of Shanghai (CN)

(73) Assignee: Johnson & Johnson Consumer Products, Inc., Skillman, NJ (US)

( * ) Notice: Subject to any disclaimer, the term of this patent is extended or adjusted under 35 U.S.C. 154(b) by 0 days.

(21) Appl. No.: 09/556,735

(22) Filed: Apr. 21, 2000

Related U.S. Application Data

(60) Provisional application No. 60/132,986, filed on May 7, 1999.

(51) Int. Cl.$^7$ ................. A61K 7/08; A61K 7/06; A61K 7/11
(52) U.S. Cl. ................. 424/70.21; 424/70.22; 424/70.1; 424/70.11; 514/881; 514/880
(58) Field of Search ............ 424/70.21, 70.11, 424/70.24, 70.14, 70.122, 70.15, 70.31; 510/422; 514/880, 881

(56) References Cited

U.S. PATENT DOCUMENTS 5,587,154 * 12/1996 Dowell et al. ............ 424/70.11
5,965,513 * 10/1999 Allan et al. ............ 510/422

FOREIGN PATENT DOCUMENTS 028459  5/1987  (EP) ............ 69/533

OTHER PUBLICATIONS

CECA ATO, Antidandruff Shampoo.
Acide N–Undecylenque, Elf Atochem.
Antidandruff–Usnate AO "A Vegetable Antidandruff Agent for Singapore and a Bactiostatic and Fungitatic Agent for Shower Preparations" Cosmetochem.
Scher Chemicals, Inc., Product Literature, 1998.
Undecylenic Derivatives Formulary for Shampoo, Lotion, Liquid Soap, Dr.V.Parison, Sep. 3, 1998, CECA ATO.
Undecylenamidopropylbetaine, A New Vegetable Based Concept for Antidandruff Treatment, CECA ATO.
AMPHORAM U, Safety Data Sheet, CECA, ATO.
AMPHORAM® U, Data Sheet, CECA, ATO.
Anti Dandruff Shampoo, Formulary, Hair Care Products, Cosmetics and Toiletries, vol. 113, 6/98.
Undecylenic Acid, Safety Data Sheet, Elf Atochem, ATO, Jul. 21, 1994.
Undecylenic Acid, Technical Information, Elf Atochem, Feb. 6, 1997.
Udeylenic Acid, Material Safety Data Sheet, May 1, 1990.
Undecylenic Acid & Its Derivatives, Elf Atochem.
Amphoram U Costmetics and Pharmacy, Elf Atochem.
Schercotaine UAB, Technial Bulletin, Jun., 1998.

\* cited by examiner

*Primary Examiner*—Thurman K. Page
*Assistant Examiner*—Blessing Fubara

(57) ABSTRACT

A composition that is useful for treating and/or ameliorating the diseases of dandruff, seborrheic dermatitis, psoriasis, and eczema and/or the symptoms associated therewith, and is non-stinging to the eyes is disclosed. The composition contains from about 0.5 weight percent to about 16 weight percent of at least one amphoteric surfactant; from about 1 weight percent to about 10 weight percent of at least one anionic surfactant; from about 0.1 weight percent to about 10 weight percent of at least one non-ionic surfactant; and from about 0.1 percent to about 15 percent active ingredient selected from Undecylenamidopropylbetaine, Undecylenic Acid, and mixtures thereof. A method for treating and/or ameliorating the diseases of dandruff, seborrheic dermatitis, psoriasis, and eczema and/or the symptoms associated therewith including topically applying an effective amount of the composition to the area desired is also disclosed.

16 Claims, No Drawings

COMPOSITION FOR TREATING AND/OR AMELIORATING THE DISEASES OF DANDRUFF, SEBORRHEIC DERMATITIS, PSORIASIS AND ECZEMA AND SYMPTOMS THEREOF

CROSS-REFERENCE TO RELATED APPLICATION

This Application claims the benefit U.S. Provisional Application No. 60/132986 filed on May 7, 1999, which is incorporated by reference herein in its entirety.

BACKGROUND OF THE INVENTION

1. Field of the Invention

The present invention relates to a composition that is useful for treating and/or ameliorating the disease of dandruff, seborrheic dermatitis, psoriasis And eczema and/or the symptoms associated therewith and has a low degree of ocular and skin irritation. More specifically, this invention is related to such compositions comprised of undecylenamidopropylbetaine and mixtures thereof with undecylenic acid which are suitable for such uses.

2. Description of the Prior Art

It is well known that many surfactants used in shampoos are irritating to the eyes, which is of particular concern in shampoos used on infants and children. As a result, several less irritating surfactants have been developed.

However, as children approach the age of puberty, hormonal changes associated with the development of scalp conditions normally associated with dandruff, such as scalp irritation and scaling, often occur. Unfortunately the active ingredients that are effective in treating such conditions are irritating to the eyes. For example, Undecylenic Acid, which is commercially available from Elf Atochem of France, and its betaine derivative, Undecylenamidopropylbetaine, which is commercially available from CECA-ATO of France under the tradename, "Amphoram U," are known as being useful for antidandruff properties in shampoos, but not without the disadvantage of eye irritancy. Therefore, there is a need for a shampoo formulation, which is not only suitable for use by children to effectively treat the skin conditions cited above, but also possesses a low degree of ocular and skin irritation.

SUMMARY OF THE INVENTION

The present invention provides a composition that is useful for treating the diseases of dandruff, seborrheic dermatitis, eczema, and psoriasis and/or the symptoms associated therewith and is non-stinging to the eyes comprising, consisting essentially of, and/or consisting of, based upon the total weight of the composition, a) from about 0.5 percent to about 16 percent of at least one amphoteric surfactant;

b) from about 1 percent to about 10 percent of at least one anionic surfactant;

c) from about 0.1 percent to about 10 percent of at least one non-ionic surfactant; and d) from about 0.1 weight percent to about 15 weight percent active ingredient.

In a second embodiment, the present invention provides a method for treating and/or ameliorating the diseases of dandruff, seborrheic dermatitis, eczema, and psoriasis and/or the symptoms associated therewith comprising, consisting essentially of, and/or consisting of: topically applying an effective amount of the detergent composition described above to an area desired.

In a third embodiment, the present invention provides a method for treating and/or ameliorating the diseases of dandruff, seborrheic dermatitis, eczema, and psoriasis and/or the symptoms associated therewith comprising, consisting essentially of, and/or consisting of: topically applying an effective amount of a detergent composition including a) from about 1 percent to about 11 percent of at least one amphoteric surfactant; b) from about 1 percent to about 8 percent of at least one anionic surfactant; c) from about 1 percent to about 10 percent of at least one non-ionic surfactant; and d) from about 3.5 percent to about 9 percent active ingredient comprised of, based upon the total weight of detergent composition, 1) from about 3 percent to about 7 percent of Undecylenamidopropylbetaine; and 2) from about 0.5 percent to about 2 percent of undecylenic acid, to an area desired.

In a fourth embodiment, the present invention provides a method for treating and/or ameliorating the diseases of dandruff, seborrheic dermatitis, eczema, and psoriasis and/or the symptoms associated therewith comprising, consisting essentially of, and/or consisting of: topically applying an effective amount of a detergent composition including a) from about 2 percent to about 10 percent of at least one amphoteric surfactant; b) from about 1 percent to about 6 percent of at least one anionic surfactant; c) from about 4 percent to about 8 percent of at least one non-ionic surfactant; and d) from about 0.8 percent to about 7 percent active ingredient comprised of, based upon the total weight of detergent composition, 1) from about 5 percent to about 6 percent of Undecylenamidopropylbetaine; and 2) from about 0.8 percent to about 1 percent of Undecylenic Acid, to an area desired.

We have unexpectedly found that the detergent composition of the present invention is not only effective in treating and/or ameliorating the diseases of dandruff, seborrheic dermatitis, eczema, and psoriasis and/or the symptoms associated therewith, but it does so with a low degree of skin and ocular irritation.

DETAILED DESCRIPTION OF PREFERRED EMBODIMENTS

The first embodiment of the present invention is directed to a detergent composition comprised of, based upon the total weight of the detergent composition, from about 0.5 percent to about 16 percent, preferably from about 1 percent to about 11 percent, and more preferably from about 2 percent to about 10 percent of at least one amphoteric surfactant; from about 1.0 percent to about 10 percent, preferably from about 1 percent to about 8 percent, and more preferably from about 1 percent to about 6 percent of at least one anionic surfactant; from about 0.1 percent to about 10 percent, preferably from about 1 percent to about 10 percent, and more preferably from about 4 percent to about 8 percent of at least one non-ionic surfactant; and from about 0.1 weight percent to about 15 weight percent, preferably from about 3.5 weight percent to about 9 weight percent, and more preferably from about 5 weight percent to about 7 weight percent of an active ingredient.

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Commercially available amphoteric surfactants suitable for use in the present invention include, but are not limited to amphocarboxylates, alkyl betaines, amidoalkyl betaines, amidoalkyl sultaines, amphophosphates, phosphobetaines, pyrophosphobetaines, carboxyalkyl alkyl polyamines, and mixtures thereof. Cocamidopropylbetaine and Lauroamphodiacetate are preferred.

Suitable anionic surfactants include, but are not limited to alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinamates; alkyl amidosulfosuccinates; alkyl carboxylates; alkyl amidoethercarboxylates; alkyl succinates; fatty acyl sarcosinates; fatty acyl amino acids; fatty acyl taurates; fatty alkyl sulfoacetates; alkyl phosphates; and mixtures thereof, wherein the alkyl group has from about 10 to about 16 carbon atoms. Preferred anionic surfactants include Sodium Laureth Sulfate 3 EO.

One class of nonionic surfactants useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Delaware under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. The alkyl glucosides have about 1 to about 6 glucose residues per molecule of alkyl glucoside.

The active ingredient suitable for use in the present invention is capable of treating the diseases of dandruff, seborrheic dermatitis, eczema, and psoriasis and/or the symptoms associated therewith while having a low degree of ocular irritancy. By "low degree of ocular irritancy" it is meant that the product is not more irritating to eyes than pure sterile water. Examples of suitable active ingredients include Undecylenamidopropylbetaine, and mixtures thereof, such as Undecylenamidopropylbetaine with, based upon the total weight of the detergent composition, from about 0 weight percent to about 2 weight percent, preferably from about 0.5 weight percent to about 2 weight percent, and more preferably from about 0.8 weight percent to about 1 weight percent Undecylenic Acid. In the latter embodiment, Undecylenamidopropylbetaine and Undecylenic Acid may be used in a weight ratio of from about 0.1 to 14:0 to 1.0, and preferably from about 5 to 6:0.8 to 1.0 Undecylenamidopropylbetaine-:Undecylenic Acid.

Optionally, the detergent compositions of this invention may also contain, based upon the total weight of the detergent composition, from about 0.01 percent to about 1.0 percent, preferably from about 0.01 percent to about 0.5 percent, and more preferably from about 0.01 to about 0.2 percent of at least one conditioning agent. Examples of suitable cationic conditioning agents nonexclusively include cationic cellulose derivatives; cationic guar derivatives; diallyldimethylammonium chloride; and mixtures thereof.

Preferably, the cationic cellulose derivative is a polymeric quaternary ammonium salt derived from the reaction of hydroxyethyl cellulose with a trimethylammonium substituted epoxide. The material known as Polyquaternium-10, commercially available from Amerchol Corporation of Edison, N.J. as "Polymer JR-400," is especially useful in this regard.

The cationic guar derivative is preferably a guar hydroxypropyltrimonium chloride, available commercially from Rhodia of Cranbury, N.J. under the tradename, "Jaguar C-17."

Other cationic conditioning polymers are those derived from the monomer diallyidimethylammonium chloride. The homopolymer of this monomer is Polyquaternium-6, which is available commercially from Allied Colloids of Suffolk, Va. under the tradename, "Salcare SC30." The copolymer of diallyldimethylammonium chloride with acrylamide is known as Polyquaternium-7, and is also available from Allied Colloids under the tradename "Salcare SC10."

In one embodiment, the conditioner portion is comprised of, based upon the overall weight of the detergent composition, from about 0.01 percent to about 0.5 percent, e.g. from about 0.01 percent to about 0.2 percent, cationic guar derivative and from about 0.01 percent to about 0.5 percent, e.g. from about 0.01 percent to about 0.2 percent, of a homopolymer or copolymer of diallyidimethylammonium chloride.

The detergent compositions of the present invention may also include one or more optional ingredients nonexclusively including a pearlescent or opacifying agent, a thickening agent, secondary conditioners, humectants, chelating agents, and additives which enhance their appearance, feel and fragrance, such as colorants, fragrances, preservatives, pH adjusting agents, and the like. The pH of the shampoo compositions of this invention is preferably maintained in the range of from about 5 to about 7.5, and more preferably from about 5.5 to about 7.0.

Commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent is present in an amount, based upon the total weight of the composition, of from about 1 percent to about 10 percent, preferably from about 1.5 percent to about 7 percent, and more preferably, from about 2 percent to about 5 percent. Examples of suitable pearlescent or opacifying agents include, but are not limited to mono or diesters of (a)

fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO—(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof.

In a preferred embodiment, the pearlescent or opacifying agent is introduced to the shampoo composition as a preformed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 (CH$_3$(CH$_2$)$_{10}$CH$_2$(OCH$_2$CH$_2$)$_4$OH) and cocamidopropyl betaine and preferably is in a weight percent ratio of from about 25 to about 30: about 3 to about 15: about 20 to about 25, respectively.

Commercially available thickening agents, which are capable of imparting the appropriate viscosity to the conditioning shampoo compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—(CH$_2$CH$_2$O)$_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Commercially available secondary conditioners, such as volatile silicones, which impart additional attributes, such as gloss to the hair are suitable for use in this invention. When used, the volatile silicone conditioning agent preferably has an atmospheric pressure boiling point less than about 220° C. The volatile silicone conditioner is present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyidisiloxane, cyclomethicone fluids such as polydimethylcyclosiloxane available commercially from Dow Corning Corporation of Midland, Mich. under the tradename, "DC-345" and mixtures thereof.

Commercially available humectants, which are capable of providing moisturization and conditioning properties to the detergent composition, are suitable for use in the present invention. The humectant is present in an amount of from about 0 percent to about 10 percent, preferably from about 0.5 percent to about 5 percent, and more preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula CH$_3$—C$_6$H$_{10}$O$_5$—(OCH$_2$CH$_2$)$_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is EDTA, and more preferably is tetrasodium EDTA, available commercially from Dow Chemical Company of Midland, Mich. under the tradename, "Versene 100XL" and is present in an amount, based upon the total weight of the composition, from about 0 to about 0.5 percent, and preferably from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent, and preferably from about 0.05 percent to about 0.10 percent.

The above described detergent composition may be prepared by combining the desired components in a suitable container and mixing them under ambient conditions in any conventional mixing means well known in the art, such as via mechanically stirred propeller, paddle, and the like. Although the order of mixing is not critical, it is preferable to pre-blend certain components, such as the fragrance and the nonionic surfactant before adding such components into the main mixture.

In embodiments wherein a cationic guar conditioner is used, the cationic guar conditioner may be preblended with glycerin under ambient conditions, followed by allowing the guar conditioner to be "wet-out" by the glycerin. Although the time to "wet-out" may vary, typically this time period may range from about 5 minutes to about 30 minutes. In this embodiment, the typical guar conditioner:glycerin weight ratio is from about 1:100 to about 1:1, e.g. from about 1:50 to about 1:5 or e.g. from about 1:15 to about 1:7. The resulting suspension may then be mixed with water under ambient conditions at a suspension:water weight ratio of from about 1:5 to about 1:20. The resulting water-suspension mixture may then be acidified with an amount of acid, preferably citric acid, effective to reduce the pH of the overall composition to a value of about 4.

In embodiments using a thickener component, the desired thickener may be preblended with from about 5 percent to about 20 percent, based upon the total weight of the composition, of water at a temperature of from about 60° C. to about 80° C. When processing with a thickener, the temperature of the overall composition may be reduced to less than about 45° C. before any pre-formed pearlizer is added thereto.

The compositions of the present invention are preferably used in shampoos, washes, baths, gels, lotions, creams, and the like for the purpose of treating the diseases of dandruff, seborrheic dermatitis, eczema, and psoriasis and/or the symptoms associated therewith.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

The following test method is used in the below Examples:
Human Ocular Irritancy Test:

This is a double-blinded, randomized, two (2) cell study, with test materials being applied once. The test material, which is a 10% dilution of a test sample having a temperature of 37–38° C., is instilled in one eye and sterile purified water is installed in the other eye of each panelist. Ten (10) panelists are required to complete the study.

Following the randomized order of testing the panelists and of assigning which material to instill and into which eye that material shall be instilled, one (1) drop of the appropriate test material is instilled into the first eye of the panelist followed by instillation of the sterile water into the second eye. A new sterile disposable eyedropper is used for each test material and disposed of after being used on only one panelist's eye. All instillations are performed either by an investigator or by a trained technician. For each eye, an independent tissue is used to blot any lacrimation that falls from that respective eye. Within 30 seconds, or as closely as possible following instillation, panelists are asked to grade stinging sensation to their eyes utilizing the following criteria: 0=within normal limits; 1=mild, very slight, 2=moderate, and 3=severe. At ¼ hour and 1 hour post-instillation, panelists are again asked to grade stinging sensation to eyes.

Example 1 and 2

Preparation of Detergent Compositions

Two formulations are prepared utilizing the materials listed in Table 1 and Table 2 below, wherein the "% w/w" column includes two appropriate ranges for a given component:

TABLE 1

Formulation of Example 1

| CTFA Name | Trade Name | Supplier, Source Country | % w/w | Function |
|---|---|---|---|---|
| Purified Water | Purified Water | In-house | 50–80 60–70 | Vehicle |
| Tetrasodium EDTA | EDTA-4Na | Yukiko, China | 0.01–1 .01–.08 | Sequestering Agent |
| Polyquaternium-10 | Polymer JR-400 | Amerchol, USA | 0.1–1 .1–.3 | Conditioning Agent |
| Guar Hydroxypropyl-trimonium Chloride | Jaguar C-17 | Rhodia, USA | 0.01–1 .01–.05 | Conditioning Agent |
| Glycerin | Glycerin | Goldschmidt, PT Sumi Asih, Indonesia | 0.1–5 | Humectant |
| Cocamidopropyl Betaine | Tegobetaine L7 | Goldschmidt, PT Sumi Asih, Indonesia | 0–15 5–10 | Secondary Surfactant |
| Undecylenamidopropyl betaine | Amphoram U | CECA-ATO, France | 1–15 5–6 | Antidandruff Active |
| Sodium Laureth Sulfate | Empicol 0251/70 | Albright & Wilson, Indonesia | 1–15 2–8 | Primary Surfactant |
| Disodium Lauroamphodi-acetate | Empigen CDL 30/J | Albright & Wilson, UK | 0.1–10 1–4 | Secondary Surfactant |
| PEG-80 Sorbitan Laurate | Atlas G-4280 | ICI, USA | 1–10 2-7 | Solubilizer |
| PEG-150 DS | PEG 6000 Distearate AT/40 | Comiel, Italy | 1–10 1–3 | Thickener |
| Quaternium-15 | Dowicil 200 | Dow Chemicals, USA | 0.01–1 .01–0.1 | Preservative |
| Cyclomethicone | DC345 Fluid | Dow Corning, USA | 0.01–2 .1–1 | Lubricant |
| FD&C Blue | FD&C Blue No. 1 Powder | Warner Jenkinson, USA | | Colorant |
| Glycol Distearate & Laureth-4 & Cocamidopropyl Betaine | Euperlan PK3000 AM | Henkel, Germany | 1–10 2–5 | Pearlizer |
| Perfume | Perfume IFF 344-AV | IFF, USA | | Fragrance |
| Citric Acid | Citric Acid Anhydrous Granular USP/FCC | Bayer, Germany | 0.01–1 .01–.1 | pH Adjuster |
| | | TOTAL | 100.000 | |

% w/w = percent on a weight to weight basis, top range is useful, bottom range is preferred

TABLE 2

Formulation of Example 2

| CTFA Name | Trade Name | Supplier, Source Country | % w/w | Function |
|---|---|---|---|---|
| Purified Water | Purified Water | In-house | 50–80; 60–70 | Vehicle |
| Tetrasodium EDTA | EDTA-4Na | Yukiko, China | 0.01–1; .01–.08 | Sequestering Agent |
| Polyquaternium-10 | Polymer JR-400 | Amerchol, USA | 0.01–1; .1–.3 | Conditioning Agent |
| Guar Hydroxypropyl-trimonium Chioride | Jaguar C-17 | Rhodia, USA | 0.01–1; .01–.05 | Conditioning Agent |
| Glycerin | Glycerin | Goldschmidt, PT Sumi Asih, Indonesia | 0.1–5; 0.1–2 | Humectant |
| Cocamidopropyl Betaine | Tegobetaine L7 | Goldschmidt, PT Sumi Asih, Indonesia | 0–15; 5–10 | Secondary Surfactant |
| Undecyienamidopropyl Betaine | Amphoram U | CECA-ATO, France | 0–15; 5–6 | Antidandruff Active |
| Sodium Laureth Sulfate | Empicol 0251/70 | Aibright & Wilson, Indonesia | 1–15; 2–8 | Primary Surfactant |
| Disodium Lauroamphodi-acetate | Empigen CDL 30/J | Aibright & Wilson, UK | 0.1–10; 1–4 | Secondary Surfactant |
| PEG-80 Sorbitan Laurate | Atlas G-4280 | ICI, USA | 1–10; 2–7 | Solubilizer |
| PEG-150 DS | PEG 6000 Distearate AT/40 | Comiel, Italy | 1–10; 1–3 | Thickener |
| Quaternium-15 | Dowicil 200 | Dow Chemicals, USA | 0.01–1; .01–0.1 | Preservative |
| Cyclomethicone | DC345 Fluid | Dow Corning, USA | 0.01–2; .1–1 | Lubricant |
| FD&C Blue | FD&C Blue No. 1 Powder | Warner Jenkinson | | Colorant |
| Glycol Distearate & Laureth-4 & Cocamidopropyl Betaine | Euperian PK3000 AM | Henkel, Germany | 1–10; 2–5 | Pearlizer |
| Perfume | IFF 344-AV | IFF, USA | | Fragrance |
| Sodium Hydroxide | Sodium Hydroxide | | 0.01–1; 0.01–.1 | pH Adjuster |
| Undecylenic Acid | Undecylenic Acid | ELF-Atochem, Canada | 0–1; 0.8–1 | Antidandruff Active |
| | | TOTAL | 100.000 | |

% w/w = percent on a weight to weight basis, top range is useful, bottom range is preferred Preparation of Preblends:
1) guar hydroxypropyltrimonium chloride/glycerin: Both ingredients are mixed together in a suitable premix vessel equipped with a mechanical agitator.
2) PEG-150 DS/undecelynic acid/PEG-80 sorbitan laurate/purified water: Water and PEG-80 sorbitan laurate are charged into a suitable jacketted kettle, then heated to a temperature of 60–65° C. PEG-150 DS is added thereto with mixing until melted/dissolved.

Preparation of Formulation of Example 1:

After EDTA-4 Na and Polyquaternium-10 are dissolved in water heated to about 55–60° C. in a suitable jacketted stainless steel vessel equipped with a propeller type mixer and sweep agitator, the guar hydroxypropyltrimonium chloride/glycerin preblend is added thereto. The resultant mixture is stirred with fast agitation until no visible lumps are present.

The PEG-150 DS/undecelynic acid/PEG-80 sorbitan laurate/purified water preblend is added thereto, followed by the sequential addition of sodium laureth sulfate, disodium lauroamphodiacetate, cocamidopropylbetaine and Undecylenamidopropylbetaine thereto. The resulting mixture is passed through a Silverson homogenizer Model 450 LS, then cooled down to 40° C.

The pH of the resulting mixture is adjusted to the desired range using a sodium hydroxide solution. While maintaining the temperature of the mixture at 40° C., Quaternium-15, perfume, the dye solution, and cyclomethicone are added thereto. The shampoo is mixed with the homogenizer for another 20 minutes at medium to fast speed. After Euperlan PK3000 AM is added thereto, the shampoo is homogenized for an additional 40 minutes. The pH is readjusted to between 5.9 and 6.4.

The formulation of Example 2 is prepared in accordance with the procedure set forth in Example 1, but using the components set forth in Table 2.

Example 1A and 2A

Preparation of Detergent Compositions

Two additional formulations comprised of the materials listed in Tables 1A and 2A below were prepared following the process set forth in Example 1 above.

TABLE 1A

| CTFA Name | Trade Name | Supplier, Source Country | % w/w | Function |
|---|---|---|---|---|
| Purified Water | Purified Water | In-house | 65.99 | Vehicle |
| Tetrasodium EDTA | EDTA-4Na | Yukiko, China | 0.07 | Sequestering Agent |
| Polyquaternium-10 | Polymer JR-400 | Amerchol, USA | 0.19 | Conditioning Agent |
| Guar Hydroxypropyl-trimonium Chloride | Jaguar C-17 | Rhodia, USA | 0.10 | Conditioning Agent |
| Glycerin | Glycerin | Goldschmidt, PT Sumi Asih, Indonesia | 1.0 | Humectant |
| Cocamidopropyl Betaine | Tegobetaine U | Goldschmidt, PT Sumi Asih, Indonesia | 7.3 | Secondary Surfactant |
| Undecylenamidopropyl betaine | Amphoram U | CECA-ATO, France | 6.0 | Antidandruff Active |
| Sodium Laureth Sulfate | Empicol 0251/70 | Albright & Wilson, Indonesia | 4.07 | Primary Surfactant |
| Disodium Lauroamphodiacetate | Empigen CDL 30/J | Albright & Wilson, UK | 2.19 | Secondary Surfactant |
| PEG-80 Sorbitan Laurate | Atlas G-4280 | ICI, USA | 6.50 | Solubilizer |
| PEG-150 distearate | PEG 6000 Distearate AT/40 | Comiel, Italy | 1.4 | Thickener |
| Quaternium-15 | Dowicil 200 | Dow Chemicals, USA | 0.05 | Preservative |
| Cyclomethicone | DC345 Fluid | Dow Corning, USA | 0.75 | Lubricant |
| FD&C Blue | FD&C Blue No. 1 Powder | Warner Jenkinson, USA | 0.0002 | Colorant |
| Glycol Distearate & Laureth-4 & Cocamidopropyl Betaine | Euperlan PK3000 AM | Henkel, Germany | 4.0 | Pearlizer |
| Perfume | Perfume IFF 344-AV | IFF, USA | 0.3 | Fragrance |
| Citric Acid | Citric Acid Anhydrous Granular USP/FCC | Bayer, Germany | 0.09 | pH Adjuster |
| | | TOTAL | 100.000 | |

TABLE 2A

| CTFA Name | Trade Name | Supplier, Source Country | % w/w | Function |
|---|---|---|---|---|
| Purified Water | Purified Water | In-house | 65.22 | Vehicle |
| Tetrasodium EDTA | EDTA-4Na | Yukiko, China | 0.07 | Sequestering Agent |
| Polyquaternium-10 | Polymer JR-400 | Amerchol, USA | 0.14 | Conditioning Agent |
| Guar Hydroxypropyl-trimonium Chloride | Jaguar C-17 | Rhodia, USA | 0.1 | Conditioning Agent |
| Glycerin | Glycerin | Goldschmidt, PT Sumi Asih, Indonesia | 1.0 | Humectant |
| Cocamidopropyl Betaine | Tegobetaine L7 | Goldschmidt, PT Sumi Asih, Indonesia | 7.3 | Secondary Surfactant |
| Undecylenamidopropyl Betaine | Amphoram U | CECA-ATO, France | 6.0 | Antidandruff Active |
| Sodium Laureth Sulfate | Empicol 0251/70 | Albright & Wilson, Indonesia | 4.07 | Primary Surfactant |

TABLE 2A-continued

| CTFA Name | Trade Name | Supplier, Source Country | % w/w | Function |
|---|---|---|---|---|
| Disodium Lauroamphodiacetate | Empigen CDL 30/J | Albright & Wilson, UK | 2.19 | Secondary Surfactant |
| PEG-80 Sorbitan Laurate | Atlas G-4280 | ICI, USA | 6.5 | Solubilizer |
| PEG-150 DS | PEG 6000 Distearate AT/40 | Comiel, Italy | 1.28 | Thickener |
| Quaternium-15 | Dowicil 200 | Dow Chemicals, USA | 0.05 | Preservative Preservative |
| Cyclomethicone | DC345 Fluid | Dow Corning, USA | 0.75 | Lubricant |
| FD&C Blue | FD&C Blue No. 1 Powder | Warner Jenkinson, USA | 0.0002 | Colorant |
| Glycol Distearate & Laureth-4 & Cocamidopropy Betaine | Euperian PK3000 AM | Henkel, Germany | 4.0 | Pearlizer |
| Perfume | Perfume IFF 344-AV | IFF, USA | 0.3 | Fragrance |
| Sodium Hydroxide | Sodium Hydroxide | J & J Export | 0.03 | pH Adjuster |
| Undecylenic Acid | Undecylenic Acid | ELF-Atochem, Canada or France | 1.0 | Antidandruff Active |
| | | TOTAL | 100.000 | |

Example 3

Efficacy Testing of the Formulations of Example 1A and Example 2A

The formulations of Example 1A and Example 2A, as well as a conditioning shampoo available from Johnson & Johnson Consumer Companies, Inc. under the tradename, "JOHNSON's KIDS Detangling Shampoo," were tested for efficacy against conditions of moderate scaling and itching possessed by children and teenagers who demonstrated such conditions prior to treatment.

A blind, single center, randomized study was performed on 285 children and teenagers between the ages of 8 and 18 years old. Each panelist was randomly placed into one of three groups of 95 members, with each group using one of the aforementioned shampoos. Panelists were seen by an investigator at a screening visit (Day −14/Visit 1), at a qualification visit (Day 1/Visit 2), at an interim visit (Day 15/Visit 3) and at completion of the treatment (Day 29/Visit 4), with "Day −14" corresponding to the first day of use of the pre-treatment (washout) shampoo.

The dosage regimen included a 14 day pre-treatment (washout) period, wherein each panelists used a shampoo available from Johnson & Johnson Consumer Companies, Inc. under the tradename, "Johnson's Baby Shampoo" three times a week, followed by a four week treatment period with the respectively assigned shampoo.

At Day 1/Visit 2, which was at the end of the 14 day pre-treatment (washout) period, the dermatologist screened prospective subjects for level of dandruff. For the dandruff evaluation, the investigator combed the subject's hair to divide the scalp into six areas, then graded each area independently for both loose and adherent dandruff scales, according to the following: 0=no scaling, 1–2=mild scaling, 3–4=moderate scaling, 5–6=marked scaling, 7–8=severe scaling, 9–10=extremely severe, heavy scaling. To qualify for the study, subjects must have had a total adherent dandruff score of eight or above. Those panelists who were eligible then proceeded with the study for an additional four weeks, following a set regimen of washing his/her hair three times per week with his/her respectively assigned shampoo starting on Day 1. The panelists returned to the clinic for an interim assessment on Day 15/Visit 3, and then for a final assessment on Day 29/Visit 4.

Clinical assessment included a dandruff evaluation by the investigator and a self-evaluation of itching by the subjects. The subjects independently self-evaluated itching of the scalp as follows: 0=none, 1=mild, 2=moderate, 3=marked (moderate/severe), 4=severe. Both scaling and itching were scored at the beginning and end of the study. The scores of all of the children were averaged. The results are summarized in Table 3.

At the end of the treatment (Day 29/Visit 4), which is four weeks after the qualification visit, a clinical global evaluation of the panelists' dandruff was conducted considering the previous dandruff ratings and using the following scale: 1=completely cleared, 2=almost completely cleared, 3=marked improvement, 4=Slight improvement, 5=no improvement. The results of the Global Evaluation (Overall Score), which is the average dandrufff score for all the panelists/formulation, are also shown in Table 3.

TABLE 3

| | Sample 3 (com'l shampoo) | Sample 1A* (Ex. 1A) | Sample 2A** (Ex. 2A) |
|---|---|---|---|
| Base Size | 95 | 95 | 95 |
| Itching Score | | | |
| Baseline | 1.83 | 1.82 | 1.66 |
| After | 0.45 | 0.46 | 0.55 |
| Reduction | 75.4% | 74.7% | 66.9% |
| Scaling Score | | | |
| Baseline | 11.12 | 10.40 | 10.8 |
| After | 4.05 | 3.22 | 2.87 |
| Reduction | 63.6% | 69.0% | 73.4% |
| Overall Score | 2.39 | 2.00*** | 2.02*** |

*includes Undecylenamidopropyl Betaine
**includes Undecylenic Acid and Undecylenamidopropyl Betaine
***Significant difference versus Sample 3 at 95% Confidence Level This Example showed that the compositions of the present invention were effective at reducing itching symptoms and were significantly more effective than the commercial shampoo in reducing scaling symptoms. Further, the overall scores for the compositions of the present inventions were significantly better than those the commercial conditioning shampoo.

Example 3A

Efficacy Testing of the Formulations of Example 1A and Example 2A

The formulations of Example 1A and Example 2A, as well as a commercial antidandruff shampoo available from The Procter & Gamble Company under the tradename, "Rejoice Antidandruff Shampoo" were tested in accordance with the test procedure set forth above in Example 3, but using a total of 56 subjects for efficacy against conditions of moderate scaling and itching possessed by children (aged 8 to 12 years old) who demonstrated such conditions prior to treatment. The results are shown in Table 4.

TABLE 4

|  | Sample 3 (Rejoice) | Sample 1A# (Ex. 1A) | Sample 2A## (Ex. 2A) |
| --- | --- | --- | --- |
| Base Size | 20 | 19 | 17 |
| Itching Score |  |  |  |
| Baseline | 1.85 | 1.47 | 1.29 |
| After | 0.60 | 0.21 | 0.12 |
| Reduction | 67.5% | 85.7% | 90.7% |
| Scaling Score |  |  |  |
| Baseline | 9.55 | 8.89 | 9.41 |
| After | 4.70 | 4.84 | 4.82 |
| % Reduction | 50.8% | 45.6% | 48.8% |
| Overall Score | 2.35 | 2.53 | 2.29 | includes Undecylenamidopropyl Betaine
includes Undecylenic Acid and Undecylenamidopropyl Betaine This Example showed that the compositions of the present invention were as effective as the commercial antidandruff shampoo in terms of reducing scaling and were more effective than the same in terms of reducing scalp itchiness.

Example 4

Ocular Irritancy Test

The human ocular sting test was also performed on the formulations prepared in accordance with Samples 1A and 2A. The results of the study are shown in Table 5.

TABLE 5

| Sample | Stinging To Eye Score |
| --- | --- |
| 1A | 0 |
| 2A | 0 |
| sterile purified water | 0 |

This Example shows that the shampoos of this invention were found to be no more stinging to the eyes than sterile purified water.

We claim:

1. A detergent composition comprising, based upon the total weight of the detergent composition:
   a) from about 0.5 percent to about 16 percent of at least one amphoteric surfactant;
   b) from about 1 percent to about 10 percent of at least one anionic surfactant;
   c) from about 0.1 percent to about 10 percent of at least one non-ionic surfactant; and
   d) from about 0.1 percent to about 15 percent active ingredient; wherein said composition is non-stinging to the eyes.

2. The detergent composition of claim 1 wherein the active ingredient is selected from Undecylenamidopropylbetaine and a mixture of Undecylenamidopropylbetaine and Undecylenic Acid.

3. The detergent composition of claim 1 wherein the active ingredient is a mixture of Undecylenamidopropylbetaine and Undecylenic Acid in a weight ratio of about 0:1 to about 15:0.

4. The detergent composition of claim 1 comprised of
   a) from about 1 percent to about 11 percent of at least one amphoteric surfactant;
   b) from about 1 percent to about 8 percent of at least one anionic surfactant;
   c) from about 1 percent to about 11 percent of at least one non-ionic surfactant; and
   d) from about 3.5 percent to about 9 percent active ingredient comprised of, based upon the total weight of detergent composition,
      1) from about 3 percent to about 7 percent of Undecylenamidopropylbetaine; and
      2) from about 0.5 percent to about 2 percent of Undecylenic Acid.

5. The detergent composition of claim 1 further comprising, based upon the total weight of the detergent composition, from about 0.01 percent to about 0.5 percent of at least one conditioning agent.

6. The detergent composition of claim 1 comprised of
   a) from about 2 percent to about 10 percent of at least one amphoteric surfactant;
   b) from about 1 percent to about 6 percent of at least one anionic surfactant;
   c) from about 4 percent to about 8 percent of at least one non-ionic surfactant; and
   d) from about 5.8 percent to about 7 percent active ingredient comprised of, based upon the total weight of detergent composition,
      1) from about 5 percent to about 6 percent of Undecylenamidopropylbetaine; and
      2) from about 0.8 percent to about 1 percent of Undecylenic Acid.

7. The detergent composition of claim 1, wherein the amphoteric surfactant is selected from the group consisting of amphocarboxylates, alkyl betaines, amidoalkyl betaines, amidoalkyl sultaines, amphophosphates, phosphobetaines, pyrophosphobetaines, carboxyalkyl alkyl polyamines, and mixtures thereof.

8. The composition of claim 1, wherein the anionic surfactant is selected from the group consisting of alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinamates; alkyl amidosulfosuccinates; alkyl carboxylates; alkyl amidoethercarboxylates; alkyl succinates; fatty acyl sarcosinates; fatty acyl amino acids; fatty acyl taurates; fatty alkyl sulfoacetates; alkyl phosphates; and mixtures thereof.

9. The composition of claim 1, wherein the nonionic surfactant is selected from the group consisting of polyoxyethylene derivatives of polyol esters, long chain alkyl glucosides, and polyglucosides.

10. The composition of claim 1, further comprising:
at least one additive selected from the group consisting of a pearlescent agent, an opacifying agent, a thickening agent, secondary conditioners, humectants, chelating agents, colorants, fragrances, preservatives, and pH adjusting agents.

11. The composition of claim 1, wherein the pH of the shampoo ranges from about 5 to about 7.5.

12. A method for treating and/or ameliorating the diseases of dandruff, seborrheic dermatitis, eczema, and psoriasis and/or the symptoms associated therewith comprising:
topically applying an effective amount of the detergent composition of claim 1 to an area desired.

13. The method of claim 12, wherein the detergent composition is mild to the skin and eyes.

14. A method for treating and/or ameliorating the diseases of dandruff, seborrheic dermatitis, eczema, and psoriasis and/or the symptoms associated therewith comprising:
topically applying an effective amount of the detergent composition of claim 4 to an area desired.

15. A method for treating and/or ameliorating the diseases of dandruff, seborrheic dermatitis, eczema, and psoriasis and/or the symptoms associated therewith comprising:
topically applying an effective amount of the detergent composition of claim 6 to an area desired.

16. A method for treating and/or ameliorating the flaking and/or scaling of skin comprising:
topically applying an effective amount of the detergent composition of claim 1 to an area desired.

* * * * *

UNITED STATES PATENT AND TRADEMARK OFFICE
CERTIFICATE OF CORRECTION

PATENT NO. : 6,333,027 B1
DATED : December 25, 2001
INVENTOR(S) : Hopkins et al.

It is certified that error appears in the above-identified patent and that said Letters Patent is hereby corrected as shown below:

Column 16,
Line 20, "1 percent to about 11 percent" should read -- 1 percent to about 10 percent --

Signed and Sealed this

Thirtieth Day of December, 2003

JAMES E. ROGAN
*Director of the United States Patent and Trademark Office*